United States Patent
Schneider et al.

(10) Patent No.: US 11,439,574 B2
(45) Date of Patent: Sep. 13, 2022

(54) DEODORANT AND PERSONAL CARE COMPOSITIONS

(71) Applicant: Rem Brands, Inc., Walton, KY (US)

(72) Inventors: David Schneider, Union, KY (US); Jonathan Schneider, Walton, KY (US)

(73) Assignee: REM BRANDS, INC., Walton, KY (US)

( * ) Notice: Subject to any disclaimer, the term of this patent is extended or adjusted under 35 U.S.C. 154(b) by 0 days.

(21) Appl. No.: 17/136,803

(22) Filed: Dec. 29, 2020

(65) Prior Publication Data

US 2021/0196597 A1    Jul. 1, 2021

Related U.S. Application Data

(60) Provisional application No. 62/955,121, filed on Dec. 30, 2019.

(51) Int. Cl.
*A61K 8/42* (2006.01)
*A61Q 15/00* (2006.01)

(52) U.S. Cl.
CPC .............. *A61K 8/42* (2013.01); *A61Q 15/00* (2013.01); *A61K 2800/48* (2013.01); *A61K 2800/77* (2013.01)

(58) Field of Classification Search
None
See application file for complete search history.

(56) References Cited

U.S. PATENT DOCUMENTS

| 4,110,428 A | 8/1978 | Kuhn |
| 2003/0162755 A1 | 8/2003 | Schneider |

(Continued)

FOREIGN PATENT DOCUMENTS

| RO | 114628 B1 | 6/1999 |
| WO | WO 2007/022453 A2 | 2/2007 |
| WO | WO 2011/143376 A1 | 11/2011 |

OTHER PUBLICATIONS

PCT- International Search Report PCT/US2020/067327, dated May 12, 2021.

*Primary Examiner* — Kyung S Chang
(74) *Attorney, Agent, or Firm* — Fay Sharpe LLP

(57) ABSTRACT

Deodorant compositions include a halo active aromatic sulfanomide compound of Formula (I): deodorant

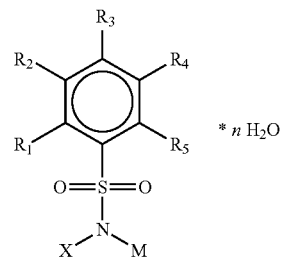

Formula (I)

wherein the variables $R_1$, $R_2$, $R_3$, $R_4$, $R_5$, X, M and n are as defined herein. The compositions can be used to deodorize surface areas of the human skin and maintain reduced microbial count over extended time periods ranging from one or two days.

20 Claims, 1 Drawing Sheet

(56) References Cited

U.S. PATENT DOCUMENTS

| | | | |
|---|---|---|---|
| 2006/0073995 A1* | 4/2006 | Schneider | A61Q 5/02 |
| | | | 510/119 |
| 2009/0227485 A1 | 9/2009 | Schneider | |
| 2011/0190229 A1* | 8/2011 | Orlow | A61K 31/35 |
| | | | 514/27 |
| 2011/0301241 A1 | 12/2011 | Schneider | |
| 2014/0170101 A1* | 6/2014 | Cetti | A61K 8/494 |
| | | | 424/65 |
| 2016/0158404 A1 | 6/2016 | Schneider | |

* cited by examiner

DEODORANT AND PERSONAL CARE COMPOSITIONS

CROSS-REFERENCE TO RELATED APPLICATIONS

This application claims priority to U.S. Provisional Patent Application Ser. No. 62/955,121, filed on Dec. 30, 2019, which is incorporated by reference in its entirety.

BACKGROUND

The present disclosure relates to deodorant compositions that can obtain extended microbial killing performance and prophylactic protection over a long period of time (hours to days). These find particular application in personal care products, particularly products used to apply the compositions to human skin.

Various bodily fluids may have an unpleasant odor (malodor) due to odor-causing molecules, which may be aliphatic, aromatic, or heterocyclic compounds containing oxygen, sulfur, or nitrogen. These odor-causing molecules can be masked using a perfume. However, it would be desirable to alter, neutralize, and/or destroy the odor-causing molecules instead. It would also be beneficial to kill the microbes that produce such odor-causing molecules, and to provide extended prophylactic protection.

A variety of deodorant and/or antiperspirant compositions for application to human skin are commercially available. Many products are made by combining active odor controlling and/or antiperspirant ingredients with waxes, oils, and/or silicones. These products are often formulated as aerosol or pump sprays, roll-on liquids, creams, emulsions, gels, gel-solids, or other solid stick formulations. For example, deodorant/antiperspirant sticks comprise a solid matrix within which an active material is contained (e.g., dissolved or suspended). These personal hygiene products are designed to provide effective perspiration and/or odor control during and after application onto the application zone (e.g. underarms, body, hands, feet, etc.).

It would be desirable to provide personal hygiene products containing compositions that can alter, neutralize, and/or destroy odor-causing molecules and that have extended microbial killing performance over longer time periods.

BRIEF DESCRIPTION

It has been found that certain halo active aromatic sulfonamide compositions can provide odor-controlling and/or extended microorganism killing performance on bodily surfaces, such as underarm skin and other parts of the human body, to which they are applied. In certain circumstances, such odor-controlling and/or residual kill performance can extend for one or more days. In addition, the halo active aromatic sulfonamides are not orally toxic, are non-irritating to the skin, and do not irritate the eyes.

Disclosed herein, in various embodiments, are personal hygiene devices comprising an odor-controlling and antimicrobial composition that can include a halo active aromatic sulfonamide compound according to Formula (I):

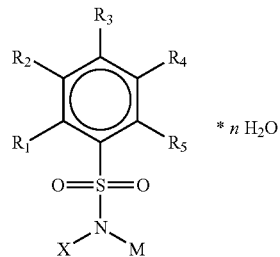

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, N(R")$_2$, substituted or unsubstituted $C_1$-$C_{18}$ alkyl, and substituted or unsubstituted aromatic;

R' is hydrogen, an alkali metal, an alkaline earth metal, substituted $C_1$-$C_{12}$ alkyl, or unsubstituted $C_1$-$C_{18}$ alkyl; and R" is hydrogen or substituted or unsubstituted $C_1$-$C_{12}$ alkyl, where the two R" groups in CON(R")$_2$ and N(R")$_2$ may be independently selected;

X is halogen;

M is an alkali or alkaline earth metal; and n is the number of water molecules per molecule of the sulfonamide compound.

The compositions include an effective amount of the sulfonamide compound, including from about 0.0001 wt % to about 5 wt % of the total composition.

These and other non-limiting features or characteristics of the present disclosure will be further described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 2:
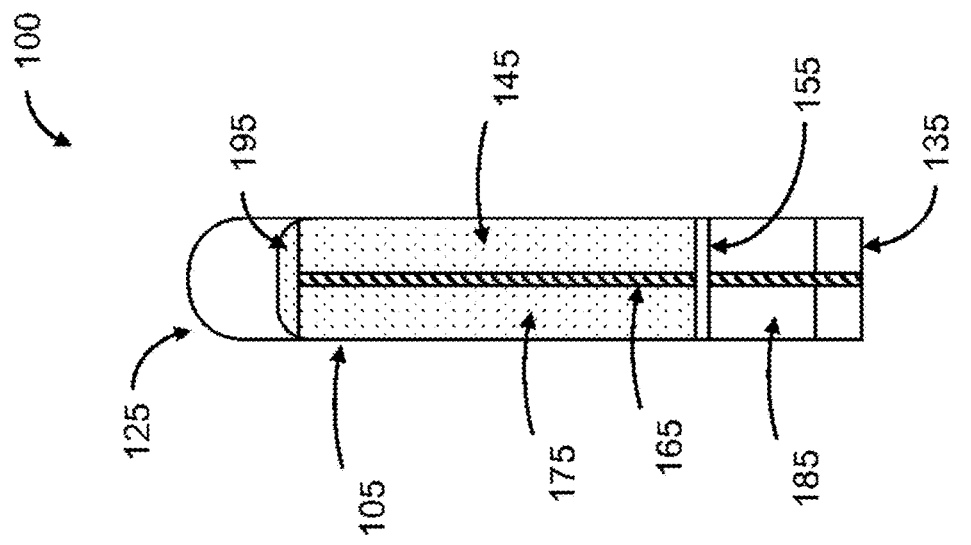
FIG. 2 is a cross-sectional view of FIG. 1 in accordance with another embodiment of the present disclosure.

A more complete understanding of the components, processes, and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Definitions

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 to 10" is inclusive of the endpoints, 2 and 10, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

The term "ambient temperature" refers to a temperature of 20° C. to 25° C.

The term "volatile" refers to materials which have a vapor pressure under ambient conditions of at least about 0.2 mm of Hg. Conversely, the term "non-volatile" as used herein refers to materials which have no measurable vapor pressure or which have a vapor of less than about 0.2 mm of Hg under ambient conditions.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, the aldehyde group —CHO is attached through the carbon of the carbonyl group.

The term "alkyl" refers to a radical composed entirely of carbon atoms and hydrogen atoms which is fully saturated. The alkyl radical may be linear, branched, or cyclic, and such radicals may be referred to as linear alkyl, branched alkyl, or cycloalkyl.

The term "aromatic" refers to a radical that has a ring system containing a delocalized conjugated pi system with a number of pi-electrons that obeys Hückel's Rule. The ring system may include heteroatoms (e.g. N, S, Se, Si, O), or may be composed exclusively of carbon and hydrogen. Exemplary aromatic groups include phenyl, thienyl, naphthyl, and biphenyl.

The term "aryl" refers to an aromatic radical composed exclusively of carbon and hydrogen. Exemplary aryl groups include phenyl, naphthyl, and biphenyl.

The term "heteroaryl" refers to an aromatic radical containing at least one heteroatom. Exemplary heteroaryl groups include thienyl. Note that "heteroaryl" is a subset of "aromatic", and is exclusive of "aryl".

The term "alkoxy" refers to an alkyl radical which is attached to an oxygen atom, i.e. —O—$C_nH_{2n+1}$, to a molecule containing such a radical.

The term "halogen" refers to fluorine, chlorine, bromine, and iodine.

The term "substituted" refers to at least one hydrogen atom on the named radical being substituted with another functional group, such as halogen, —CN, or —$NO_2$. Besides the aforementioned functional groups, an aromatic group may also be substituted with alkyl or alkoxy. An exemplary substituted aryl group is methylphenyl.

The term "alkali metal" refers to lithium, sodium, and potassium.

The term "alkaline earth metal" refers to magnesium and calcium.

The terms "article" and "device" are used to refer to an item or object, and should not be construed as limiting such items due to size. It is specifically contemplated that smaller items can be assembled to form a larger item, and both the small and large items will be referred to herein as "articles" and/or "devices".

The term "stick" as used herein refers to a material that is firm to the touch, which is often in the shape of a rod or bar. A stick is commonly housed in a container comprising a barrel having an open end and a piston for pushing the stick up the barrel through the open end, and the stick retains its shape and integrity during its expulsion.

Compositions

Halo active aromatic sulfonamide organic compounds are useful for reducing or eliminating odor. Chloramine-T is an example of a sulfonamide organic compound that has the ability to release an active chloride ion when needed on demand, immediately after which it simultaneously generates an active aromatic sulfo nitrene companion ion. The chlorine atom has a +1 formal charge in a hypochlorite ion, $ClO^-$, which is the form taken by the chlorine atom when dissociated from the sulfonamide compound. Reference to the chlorine atom as having a +1 or $1^-$ charge may be used in this application interchangeably because this terminology has no effect on the compound itself or its use.

It has been found in the present disclosure that halo active aromatic sulfonamide organic compounds have an antimicrobial performance when applied to human skin that can extend over long periods of time. In particular hydrates of halo active aromatic sulfonamide organic compounds will continue to exhibit antimicrobial ability over long time periods, such as over 24 hours, over 48 hours, over 72 hours, or even as long as 168 hours. The halo active aromatic sulfonamide organic compounds also offer residual odor elimination when dry; have excellent stability, with a shelf life measured in years; and have extremely low toxicity, are not skin irritating, and are not a sensitizer. These qualities are useful in personal hygiene products and devices, particularly in deodorants.

The present disclosure thus relates to deodorant compositions for personal care products and personal hygiene products. The deodorant compositions of the present disclosure comprise (A) a halo active aromatic sulfonamide compound, as described further herein; and (B) a carrier. The compositions can also include (C) a thickener; (D) one or more additional active ingredients, particularly an antiperspirant; and/or (E) one or more additional additives. Such additives may include an emollient, a bulking agent, and/or a fragrance. In some embodiments, the deodorant composition may also include (F) a propellant. The compositions disclosed herein may also include any combination of two or more of these components.

The halo active aromatic sulfonamide compound used in the deodorant compositions of the present disclosure has the structure of base Formula (I):

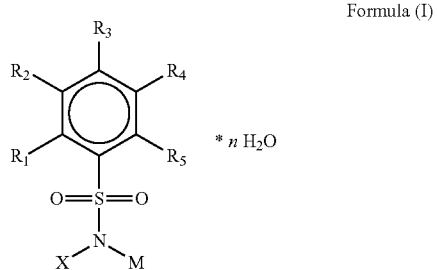

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, N(R")$_2$, substituted or unsubstituted $C_1$-$C_{18}$ alkyl, and substituted or unsubstituted aromatic;

R' is hydrogen, an alkali metal, an alkaline earth metal, substituted $C_1$-$C_{12}$ alkyl, or unsubstituted $C_1$-$C_{18}$ alkyl; and R" is hydrogen or substituted or unsubstituted $C_1$-$C_{12}$ alkyl, where the two R" groups in CON(R")$_2$ and N(R")$_2$ may be independently selected;

X is halogen;

M is an alkali or alkaline earth metal; and n is the number of water molecules per molecule of the sulfonamide compound.

Again, the term "aromatic", as used herein, does not refer to a smell detected by the nose.

Generally, M is sodium or potassium. X is generally chlorine, bromine, fluorine, or iodine, and in particular embodiments is chlorine. Compounds of Formula (I) may or may not be hydrated, as indicated by the variable n. In particular embodiments, the compounds of Formula (I) are a trihydrate (i.e., n=3) or a hexahydrate (i.e. n=6). In other embodiments, the compound is in a solid form, such as a powder.

When the phenyl and/or alkyl group is substituted, one or more hydrogen atoms may be independently replaced with hydroxyl or halogen.

In particular embodiments of Formula (I), $R_3$ is methyl, COOH, or COOM$_1$; $R_1$, $R_2$, $R_4$, and $R_5$ are independently selected from hydrogen, COOH, COOM$_1$, COOR', CON(R")$_2$, alkoxy, CN, NO$_2$, SO$_3$R", halogen, substituted or unsubstituted phenyl, sulfonamide, halosulfonamide, N(R")$_2$, substituted or unsubstituted $C_1$-$C_{18}$ alkyl, and substituted or unsubstituted aromatic; X is halogen; M$_1$ is an alkali or alkaline earth metal; and n is the number of water molecules per molecule of the sulfonamide compound.

In further embodiments, $R_3$ is methyl, COOH, or COOM$_1$; $R_1$, $R_2$, $R_4$, and $R_5$ are independently selected from hydrogen, COOH, COOM$_1$, COOR', CON(R")$_2$, alkoxy, CN, NO$_2$, SO$_3$R", halogen, substituted or unsubstituted phenyl, sulfonamide, halosulfonamide, N(R")$_2$, substituted or unsubstituted $C_1$-$C_{18}$ alkyl, and substituted or unsubstituted aromatic; X is halogen; M is an alkali or alkaline earth metal; n is the number of water molecules per molecule of the sulfonamide compound; and at least one of $R_1$, $R_2$, $R_4$, and $R_5$ is not hydrogen.

In yet other embodiments of Formula (I), $R_3$ is selected from COOH, COOM$_1$, COOR', CON(R")$_2$, CN, NO$_2$, halogen, and substituted or unsubstituted $C_2$-$C_{12}$ alkyl; $R_1$, $R_2$, $R_4$, and $R_5$ are independently selected from hydrogen, COOH, COOM$_1$, COOR', CON(R")$_2$, alkoxy, CN, NO$_2$, SO$_3$R", halogen, substituted or unsubstituted phenyl, sulfonamide, halosulfonamide, N(R")$_2$, substituted or unsubstituted $C_1$-$C_{18}$ alkyl, and substituted or unsubstituted aromatic; X is halogen; M is an alkali or alkaline earth metal; and n is the number of water molecules per molecule of the sulfonamide compound.

In still other embodiments of Formula (I), $R_1$, $R_2$, $R_3$, $R_4$, and $R_5$ are independently selected from hydrogen, COOH, COOM$_1$, NO$_2$, halogen, N(R")$_2$, substituted or unsubstituted $C_1$-$C_{18}$ alkyl, and substituted or unsubstituted aromatic; X is halogen; M is an alkali or alkaline earth metal; and n is the number of water molecules per molecule of the sulfonamide compound.

In yet other embodiments of Formula (I), $R_2$ and $R_4$ are identical to each other; and $R_1$, $R_3$, and $R_5$ are hydrogen.

In yet other embodiments of Formula (I), $R_2$ and $R_4$ are hydrogen; and $R_1$, $R_3$, and $R_5$ are identical to each other.

In more specific embodiments of Formula (I), $R_3$ is selected from COOH, COOM$_1$, COOR', and CON(R")$_2$. Most desirably, $R_3$ is COOH or COOM$_1$, while $R_1$, $R_2$, $R_4$, and $R_5$ are hydrogen.

In other embodiments of Formula (I), $R_1$, $R_2$, $R_3$, $R_4$, and $R_5$ are independently selected from hydrogen, COOH, COOM$_1$, COOR', CON(R")$_2$, NO$_2$, halogen, N(R")$_2$, substituted or unsubstituted $C_1$-$C_{18}$ alkyl, and substituted or unsubstituted aromatic; wherein at least one of $R_1$, $R_2$, $R_3$, $R_4$, and $R_5$ is not hydrogen; X is halogen; M is an alkali or alkaline earth metal; and n is the number of water molecules per molecule of the sulfonamide compound.

In still other embodiments of Formula (I), $R_3$ is COOH or COOM$_1$; $R_1$, $R_2$, $R_4$, and $R_5$ are independently selected from hydrogen, NO$_2$, halogen, N(R")$_2$, substituted or unsubstituted $C_1$-$C_{18}$ alkyl, and substituted or unsubstituted aromatic; X is halogen; M is an alkali or alkaline earth metal; and n is the number of water molecules per molecule of the sulfonamide compound. In further specific embodiments, at least one of $R_1$, $R_2$, $R_4$, and $R_5$ is not hydrogen.

In some embodiments of Formula (I), at least one of $R_1$, $R_2$, $R_3$, $R_4$, or $R_5$ are not hydrogen. In more specific embodiments of Formula (I), at least two of $R_1$, $R_2$, $R_3$, $R_4$, or $R_5$ are not hydrogen. In other words, the benzene ring contains the sulfonamide substituent and an additional one or two other substituents.

In more specific embodiments of Formula (I), the halo active aromatic sulfonamide compound has the structure of Formula (II):

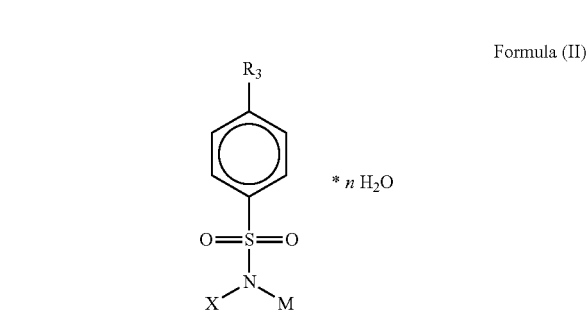

Formula (II)

wherein $R_3$ is COOR'; R' is hydrogen, an alkali metal, an alkaline earth metal, substituted $C_1$-$C_{18}$ alkyl, unsubstituted $C_1$-$C_{18}$ alkyl, substituted aromatic, or unsubstituted aromatic; X is halogen; M is an alkali or alkaline earth metal; and n is the number of water molecules per molecule of the sulfonamide compound. The N-chloro-4-carboxybenzenesulfonamide compound of Formula (II) is also referred to herein as BENZ. BENZ exhibits a lower chlorine smell than chloramine-T or chloramine-B. When BENZ is combined with at least one fragrance, there is no detectable chlorine smell for most humans. BENZ is also known as monalazone disodium, CAS #61477-95-0.

Two particular sulfonamide compounds contemplated for use are N-chloro-p-toluenesulfonamide (i.e. chloramine-T) and N-chloro-4-carboxybenzenesulfonamide (i.e. BENZ). These two compounds are shown below as Formulas (III) and (IV):

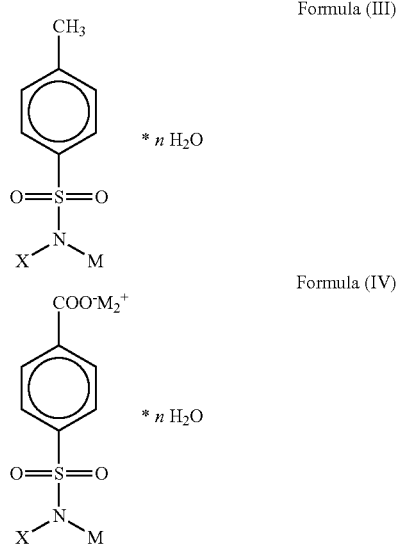

wherein $M_2$ is hydrogen, an alkali metal, or an alkali earth metal; X is halogen, M is independently an alkali or alkaline earth metal; and n is the number of water molecules per molecule of each sulfonamide compound. Desirably, $M_2$ is hydrogen, sodium, or potassium.

In other particular embodiments, one or more of $R_1$, $R_2$, $R_3$, $R_4$, and $R_5$ are substituted with —COOR' (and the others are hydrogen). In this regard, it is believed that when the halo active aromatic sulfonamide compound has two or more ionic charges, that the compound has higher antimicrobial performance.

The halo active aromatic sulfonamide compounds of base Formula (I) are stable and do not decompose, permitting the deodorant composition to have a long shelf life. The compounds of Formula (I) are also very soluble in water, low in toxicity, and have minimal bleach odor.

The halo active aromatic sulfonamide compound (A) is generally present in the deodorant composition in the amount of about 0.0001 wt % to about 5 wt %. In particular embodiments, the sulfonamide compound may be present in the deodorant composition in the amount of about 0.001 to about 2 wt %, or from about 0.01 to about 1 wt %.

The deodorant composition also comprises one or more carriers (B). The sulfonamide compound (A), along with any other active ingredients, are dissolved or suspended in the carrier. The carrier is typically a fluid, such as water and/or a water-immiscible oil. Typically, the carrier comprises either no polar liquid or very little polar liquid that can form a liquid phase with the water-immiscible oil or oil mixture. In particular, water is typically present in the deodorant composition as a hydrate with the sulfonamide compound (A) and also with other active ingredients.

The carrier (B) can be volatile or non-volatile, or a mixture of carriers. Examples of suitable carriers include a volatile silicone compound or an aliphatic hydrocarbon. These volatile silicone compounds may be cyclic, linear or branched chain silicones. The aliphatic hydrocarbon may have from about 10 to about 32 carbon atoms, including from about 10 to about 20 carbon atoms. Examples of non-volatile carriers include silicone oils such as siloxanes. Aliphatic or aromatic esters containing long chain alkyl groups can also be used as the carrier. Desirably, such esters have a low melting point below room temperature. Examples include alkyl benzoates or dibenzoates, which can be alkoxylated or polyalkoxylated, and which typically contain a minimum of 8 carbon atoms. Other suitable carriers include aliphatic alcohols which typically contain at least 10 carbon atoms, such as decanol or benzyl alcohol. The one or more carriers (B) together can comprise from about 5 wt % to about 99.9 wt % of the deodorant composition.

The deodorant composition may comprise one or more thickeners (C). Thickeners are used to increase the viscosity of the deodorant composition or to transform the composition from a liquid to a semi-solid or solid state. They are contemplated when the deodorant composition will eventually take the form of a solid, a semi-solid, or a gel.

One example of a thickener is a gellant or gelling agent. The gelling agent forms a matrix in which the sulfonamide compound (A) and other ingredients are suspended. The gelling agent can be a natural or synthetic wax. For example, suitable natural waxes may include petroleum-derived waxes such as paraffins, as well as animal and plant waxes. Suitable synthetic waxes may include various polymers such as polyethylene. Other gelling agents may also include, for example, natural or synthetic hydrogenated oils or fats, fatty acids, fatty alcohols, salts of fatty acids, hydroxy fatty acids, fatty acid esters, a stearyl alcohol, cetyl alcohol, hydrogenated castor oil, and glyceryl stearate. The gelling agent may be a high melting point wax, such as beeswax, montan, ozocerite, ceresin, paraffin, or synthetic wax. In other embodiments, the gelling agent may be a low melting point wax, such as a fatty alcohol containing from about 8 to about 25 carbon atoms. The gelling agent may comprise derivatives of carboxylic acids, including amide derivatives of carboxylic acids such as hydroxystearic acids. In still further embodiments, the gelling agent may be a silicone wax.

Other organic or inorganic thickeners can include silicates; clays such as bentonite or montmorillonite; carbohydrates or polysaccharides such as dextrins; polymers such as styrene block copolymers; polyamides; polysiloxanes; sterols; or cellulose. Polyalkylene glycols are also useful as thickeners.

Of course, any combination of two or more thickeners may be used as well. The thickener(s) can be present in the deodorant composition in the amount of about 1 wt % to about 35 wt %.

The deodorant composition may also include one or more active ingredients (D) in addition to the halo active aromatic sulfonamide compound (A). In particular embodiments, it is contemplated that an antiperspirant (D1) is also present in the deodorant composition. The antiperspirant may be an astringent active salt, or can also be, for example, aluminum, zirconium, mixed aluminum/zirconium salts, inorganic salts, salts with organic anions, aluminium halides and halohydrate salts, and/or zirconium halides and halohydrate salts. In specific embodiments, the antiperspirant is aluminum chlorohydrate, aluminum chloride, aluminum sulfate, and aluminum zirconium complexes (e.g., aluminum zirconium tetrachlorohydrex glycine). The one or more additional active ingredients may be activated (e.g., activated aluminum chlorohydrate).

In some embodiments, the one or more active ingredients (D) have a particle size range of about 0.1 μm to about 200 μm. The deodorant composition may comprise from about 1 wt % to about 35 wt % of the one or more additional active ingredients (D).

The composition may also include various other additives (E). Such additives may include, for example, a buffering agent (E1); a surfactant (E2); or a perfume or fragrance (E3).

For stability and for optimum performance, the pH of the deodorant composition may be between 6 and 14, though generally the pH should be kept between 6 and 10, or between 7 and 9. A buffering agent (E1) can be included to maintain the pH within these pH ranges. Exemplary buffering agents include sodium bicarbonate, potassium bicarbonate, sodium carbonate, potassium carbonate, acetate buffers (such as sodium acetate), phosphate buffers (such as tri and di sodium phosphate and mixtures thereof, pH blended phosphates, sulfate buffers (such as di and tri sodium sulfate), and mixtures thereof. The buffering agent can be added in desired amounts. In certain embodiments, the deodorant composition may include from about 0.0001 wt % to about 5 wt % of a buffering agent (E1). In further embodiments, the preferred weight ratio of the sulfonamide compound to the buffering agent is from about 50:1 to about 1:1, or from about 50:1 to about 2:1, or from about 20:1 to about 2:1. The preferred buffering agent is sodium bicarbonate. However, in some specific embodiments, a buffering agent (E1) is not used.

A surfactant (E2), or wetting agent, can also be added to the deodorant composition. The surfactant decreases surface tension, allowing the sulfonamide compound (A) to be spread more widely when applied, and also assisting in the removal of the composition from skin or clothing. Both non-ionic and anionic surfactants can be used. Examples of nonionic surfactants include esters or ethers containing a $C_8$ to $C_{22}$ alkyl moiety and a hydrophilic moiety which can comprise a polyoxyalkylene group (POE or POP) and/or a polyol. However, in some specific embodiments, a surfactant is not used. The surfactant (E2) can be present in the deodorant composition in the amount of about 0.0001 wt % to about 10 wt %.

A perfume or fragrance (E3) can also be included in the deodorant composition if desired. These are also used to mask any remaining odor. Examples of fragrances may include anisole; furfural; citronellal; and terpenes. The perfume/fragrance (E3) can be present in the deodorant composition in the amount of about 0.0001 wt % to about 5 wt % of the deodorant composition.

Also contemplated are additional additives (E) such as skin feel improvers like talc or finely divided polyethylene; moisturizers such as glycerol; skin benefit agents such as allantoin or lipids; skin cooling agents such as an alcohol, menthol, and/or menthol derivative, and/or colorants. The total amount of these additional additives ranges from 0.0001 wt % to about 10 wt % of the deodorant composition.

It is contemplated that the deodorant composition can be dispensed as an aerosol, and in such cases a propellant (F) is also present. Examples of suitable propellants include halogenated hydrocarbons, hydrocarbons, air, nitrogen, carbon dioxide, and other appropriate gases. The propellant can be from about 30 wt % to about 95 wt % of the composition.

While not being limited by theory, it is believed that minor amounts of water, either through the hydrated nature active sulfonamide compound and/or the ambient humidity, will keep the sulfonamide active over an extended period of time. Thus, the antimicrobial kill performance of the sulfonamide will extend over that time period as well, so that new microorganism growth will also be eliminated. Extended kill and prophylactic protection of is thus possible.

In accordance with additional aspects of the present disclosure, deodorizing compositions containing a halo active aromatic sulfonamide compound may be embodied as a personal care product, such as a shower gel (i.e., body wash).

In particular embodiments, a shower gel or body wash composition includes: (A) the halo active aromatic sulfonamide compound; (B) an aqueous carrier; (C) one or more surfactants; and (D) additional additives.

The shower gel or body wash composition include a halo active aromatic sulfonamide compound (A), as described above, in an amount of from about 0.01 wt % to about 99.9 wt % of the composition, or from about 1 wt % to about 50 wt % of the composition, or from about 10 wt % to about 25 wt % of the composition.

The shower gel or body wash compositions are in the form of a pourable liquid (under ambient conditions), and include an aqueous carrier (B). The aqueous carrier may form the balance of the composition. In specific embodiments, the aqueous carrier may be present in the composition in an amount of from about 20 wt % to about 99.9 wt %, or from about 20 wt % to about 95 wt %, or from about 50 wt % to about 95 wt %, or from about 60 wt % to about 85 wt %.

The aqueous carrier (B) may comprise water, or a miscible mixture of water and organic solvent, and in one aspect may comprise water with minimal or no significant concentrations of organic solvent, except as otherwise incidentally incorporated into the composition as other components. In particular embodiments, the aqueous carriers in the present composition includes water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

The shower gel/body wash composition may comprise from about 10 wt % to about 50 wt % of one or more surfactants (C). In some embodiments, the surfactants may be anionic surfactants, zwitterionic surfactants, amphoteric surfactants, and combinations thereof.

The shower gel/body wash compositions disclosed herein may also include one or more additional additives (D) in an amount ranging from about 0.01 wt % to about 50 wt % of the total composition, including from about 1 wt % to about 10 wt %. For example, the additional additives may include, but are not limited to, perfumes or fragrances, coloring agents or dyes, hair bleaching agents, thickeners, moisturizers, emollients, pharmaceutical actives, vitamins or nutrients, anti-dandruff agents, hair perming agents, hair growth or restorer agents, and similar other materials.

Articles/Personal Hygiene Devices

The deodorant compositions of the present disclosure can be applied topically to various parts of the human body by, for example, spraying, as a liquid, as a foam, as a gel, and/or as a semi-solid gel. As a result, these compositions can take forms such as solid sticks, roll-on suspensions or solutions, gels, creams, emulsions, etc. They can be dispensed as a stick, via a wipe, through a pump, or as an aerosol.

Figure 1:
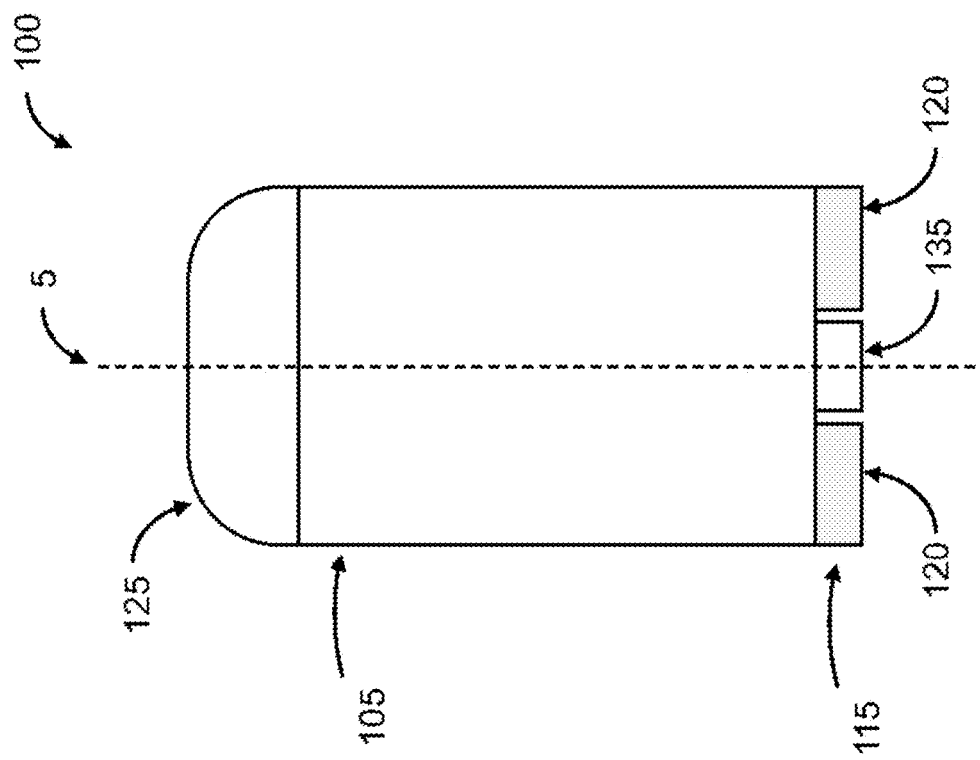
FIG. 1 is an exterior view of a personal hygiene device in accordance with one embodiment of the present disclosure.

In preferred embodiments, the deodorant composition is formulated as a solid or a gel, such as is commonly sold in the form of a deodorant stick. With reference to FIG. 1, such a personal hygiene device 100 is illustrated. The device 100 includes a hollow body 105, a base 115, and a removable cap 125. The base 115 may include a movable portion 135, which moves relative to the body 105. The base 115 may also include stationary portions 120.

With reference to FIG. 2, a cross-section of the device 100 along line 5 is shown. The deodorant composition 145 may be formulated as a gel or semi-solid gel contained within an occupied portion 175 of the hollow body 105. The deodorant composition 145 may rest on a platform 155, which is connected to a spindle 165. The spindle 165 connects the platform 155 to the movable portion 135 of the base 115. In particular embodiments, a user of the device 100 may twist the movable portion 135, thereby raising and/or lowering the platform 155 relative to the base 115. In other words, as the movable portion 135 is rotated relative to the body 105, the platform 155 is raised or lowered along the spindle 165, thereby increasing the empty portion 185 (i.e. decreasing the amount of the deodorant composition within the occupied portion 175), or vice versa. As the platform 155 is moved away from the base 115, a portion of the deodorant composition 195 is exposed. A user may remove the removable cap 125, and thereby apply the exposed deodorant composition 195 to a portion of their skin.

Methods

Also disclosed herein are methods of using a personal care compositions to, for example, deodorize and/or cleanse the body of a person or an animal. In particular embodiments, a method of deodorizing and cleansing the skin or hair with a personal care composition is provided, wherein the method includes the step of applying the composition to the skin or hair. In further embodiments, the method also includes the step of rinsing off the composition with water.

The present disclosure has been described with reference to exemplary embodiments. Modifications and alterations will occur to others upon reading and understanding the preceding detailed description. It is intended that the present disclosure be construed as including all such modifications and alterations insofar as they come within the scope of the appended claims or the equivalents thereof.

The invention claimed is:
1. A personal care deodorant composition, comprising:
a halo active aromatic sulfonamide compound of Formula (I):

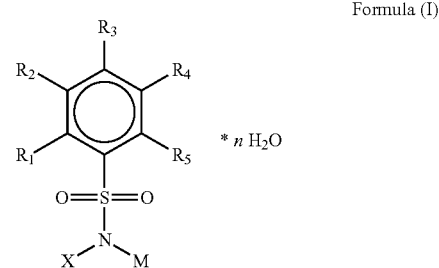

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, N(R")$_2$, substituted or unsubstituted $C_1$-$C_{18}$ alkyl, and substituted or unsubstituted aromatic;
R' is hydrogen, an alkali metal, an alkaline earth metal, substituted $C_1$-$C_{18}$ alkyl, or unsubstituted $C_1$-$C_{18}$ alkyl; and
R" is hydrogen or substituted or unsubstituted $C_1$-$C_{12}$ alkyl, where the two R" groups in CON(R")$_2$ and N(R")$_2$ may be independently selected;
X is halogen; and
M is an alkali or alkaline earth metal;
a carrier for the sulfonamide compound;
a thickener; and
an antiperspirant;
wherein the deodorant composition is in the form of a solid stick.
2. The composition of claim 1, wherein the halo active aromatic sulfonamide compound is N-chloro-4-carboxybenzenesulfonamide.
3. The composition of claim 1, wherein the halo active aromatic sulfonamide compound is present in the deodorant composition in an amount of about 0.0001 wt % to about 5 wt %.
4. The composition of claim 1, wherein the thickener is a wax, hydrogenated oil or fat, fatty acid, fatty alcohol, fatty acid ester, an alcohol, hydrogenated castor oil, glyceryl stearate, a derivative of a carboxylic acid, a silicate, a clay, a carbohydrate or polysaccharide, a polymer, a sterol, cellulose, or a polyalkylene glycol; and
wherein the thickener comprises from about 1 wt % to about 35 wt % of the deodorant composition.
5. The composition of claim 1, wherein the antiperspirant comprises aluminum chlorohydrate, aluminum chloride, aluminum sulfate, an aluminum zirconium complex, or activated aluminum chlorohydrate.
6. The composition of claim 1, further comprising a buffering agent.
7. The composition of claim 6, wherein the buffering agent comprises sodium bicarbonate, potassium bicarbonate, sodium carbonate, potassium carbonate, an acetate buffer, a phosphate buffer, a pH blended phosphate, or a sulfate buffer.
8. The composition of claim 1, further comprising a surfactant.
9. The composition of claim 8, wherein the surfactant comprises from about 0.0001 wt % to about 10 wt % of the deodorant composition.

10. The composition of claim 1, further comprising a perfume or fragrance.

11. The composition of claim 10, wherein the perfume or fragrance comprises from about 0.0001 wt % to about 5 wt % of the deodorant composition.

12. The composition of claim 1, further comprising a skin feel improver, a moisturizer, a skin benefit agent, or a skin cooling agent.

13. A method of deodorizing and cleansing skin with a personal care composition, the method comprising:
    applying the personal care composition to the skin;
    wherein the personal care composition includes:
        a halo active aromatic sulfonamide compound of Formula (I):

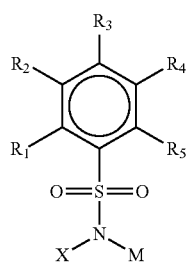

Formula (I)

wherein $R_1$, $R_2$, $R_3$, $R_4$, and $R_5$ are independently selected from hydrogen, COOR', $CH_3$, $CON(R")_2$, alkoxy, CN, $NO_2$, $SO_3R"$, halogen, substituted or unsubstituted phenyl, sulfonamide, halosulfonamide, $N(R")_2$, substituted or unsubstituted $C_1$-$C_{18}$ alkyl, and substituted or unsubstituted aromatic;

R' is hydrogen, an alkali metal, an alkaline earth metal, substituted $C_1$-$C_{18}$ alkyl, or unsubstituted $C_1$-$C_{18}$ alkyl; and R" is hydrogen or substituted or unsubstituted $C_1$-$C_{12}$ alkyl, where the two R" groups in $CON(R")_2$ and $N(R")_2$ may be independently selected;

X is halogen; and

M is an alkali or alkaline earth metal;

wherein the personal care composition further includes a thickener and an antiperspirant; and wherein the personal care composition is in the form of a solid stick.

14. The method of claim 13, wherein the personal care composition further includes one or more surfactants.

15. A personal care deodorant composition, comprising:
    a halo active aromatic sulfonamide compound of Formula (I):

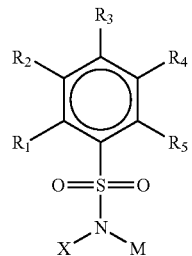

Formula (I)

wherein $R_1$, $R_2$, $R_3$, $R_4$, and $R_5$ are independently selected from hydrogen, COOR', $CON(R")_2$, alkoxy, CN, $NO_2$, $SO_3R"$, halogen, substituted or unsubstituted phenyl, sulfonamide, halosulfonamide, $N(R")_2$, substituted or unsubstituted $C_1$-$C_{18}$ alkyl, and substituted or unsubstituted aromatic;

R' is hydrogen, an alkali metal, an alkaline earth metal, substituted $C_1$-$C_{18}$ alkyl, or unsubstituted $C_1$-$C_{18}$ alkyl; and R" is hydrogen or substituted or unsubstituted $C_1$-$C_{12}$ alkyl, where the two R" groups in $CON(R")_2$ and $N(R")_2$ may be independently selected;

X is halogen; and

M is an alkali or alkaline earth metal;

a non-aqueous carrier for the sulfonamide compound;

a thickener; and an antiperspirant; and wherein the personal care deodorant composition is in the form of a solid stick.

16. The composition of claim 1, wherein the carrier comprises from about 5 wt % to about 99.9 wt % of the deodorant composition.

17. The composition of claim 1, wherein the carrier comprises water and at least one of a volatile silicone compound, an aliphatic hydrocarbon, an aliphatic or aromatic ester, or an aliphatic alcohol.

18. The composition of claim 1, wherein the antiperspirant comprises from about 1 wt % to about 35 wt % of the deodorant composition.

19. The composition of claim 6, wherein the buffering agent is present in an amount such that the deodorant composition has a pH between 6 and 14.

20. The composition of claim 6, wherein the buffering agent comprises from about 0.0001 wt % to about 5 wt % of the deodorant composition.

* * * * *